United States Patent
Harttig

(10) Patent No.: US 6,746,874 B2
(45) Date of Patent: Jun. 8, 2004

(54) REAGENT PREPARATION CONTAINING MAGNETIC PARTICLES IN TABLET FORM

(75) Inventor: Herbert Harttig, Altrip (DE)

(73) Assignee: Roche Diagnostics, GmbH, Penzberg (DE)

(*) Notice: Subject to any disclaimer, the term of this patent is extended or adjusted under 35 U.S.C. 154(b) by 321 days.

(21) Appl. No.: 09/893,533

(22) Filed: Jun. 29, 2001

(65) Prior Publication Data

US 2001/0046714 A1 Nov. 29, 2001

Related U.S. Application Data

(62) Division of application No. 08/870,385, filed on Jun. 6, 1997, now Pat. No. 6,274,386.

(30) Foreign Application Priority Data

Jun. 7, 1996 (DE) .......................... 196 22 885

(51) Int. Cl.$^7$ ............................. G01N 33/553
(52) U.S. Cl. ................ 436/526; 436/518; 435/7.5; 435/180; 424/1.25; 424/1.29; 424/465; 424/470; 424/489; 514/961
(58) Field of Search ................ 436/526, 518; 435/7.5, 180; 424/1.25, 1.29, 465, 470, 489; 514/961

(56) References Cited

U.S. PATENT DOCUMENTS

| | | |
|---|---|---|
| 3,981,776 A | 9/1976 | Saxholm |
| 4,115,534 A | 9/1978 | Ithakissios ............. 424/1 |
| 4,169,804 A | 10/1979 | Yapel, Jr., et al. |
| 4,233,169 A | 11/1980 | Beall et al. ............. 252/62 |
| 4,343,901 A | 8/1982 | De Filippi |
| 4,483,920 A | 11/1984 | Gillespie et al. ........... 435/6 |
| 4,712,310 A | 12/1987 | Roy |
| 4,735,796 A | 4/1988 | Gordon |
| 4,820,627 A | 4/1989 | McGeehan |
| 5,009,994 A | 4/1991 | McGeehan |
| 5,234,809 A | 8/1993 | Boom et al. ............. 435/91 |
| 5,512,439 A | 4/1996 | Hornes et al. |
| 5,593,824 A | 1/1997 | Tremi et al. |
| 5,597,531 A | 1/1997 | Liberti et al. |
| 5,746,999 A | 5/1998 | Gries et al. |

FOREIGN PATENT DOCUMENTS

| | | |
|---|---|---|
| DE | 44 06 139 | 8/1985 |
| DE | 195 20 398 | 12/1996 |
| EP | 345897 A3 | 5/1989 |
| JP | 4-323560 | 11/1992 |

OTHER PUBLICATIONS

Fujimori et al, International Journal of Phamraceuticals 119, (1995) pp. 47–55, "Effect of magnetically controlled gastrice residence of sustained release tablets on bioavailability of acetaminophen".

Fujimori et al, S.T.P. Pharma Sciences 4 (6) 425–439, 1994, "Preparation of a magnetically-responsive tablet and confirmation of its gastric residence in beagle dogs".

International Publication No. WO 90/06045 published Jun. 14, 1990.

Marko et al., Analytical Biochemistry, vol. 121, No. 2, Apr. 1982, pp. 382–387, A Procedure for the Large–Scale Isolation of Highly Purified Plasmid DNA Using Alkaline Extraction and Binding.

Vogelstein et al., Proc. Natl. Acad. Sci., vol. 76, No. 2, pp 615–619, Feb. 1979, "Preparation and analytical purification of DNA from agarose".

*Primary Examiner*—Christopher L. Chin
*Assistant Examiner*—Pensee T. Do
(74) *Attorney, Agent, or Firm*—Arent Fox Kintner Plotkin & Kahn, PLLC

(57) ABSTRACT

Subject matter of the invention is a reagent preparation for binding components of a sample in the form of a tablet comprising a multitude of magnetic particles which are held together with the aid of excipients, and the use of this reagent preparation in analytical test.

6 Claims, No Drawings

REAGENT PREPARATION CONTAINING MAGNETIC PARTICLES IN TABLET FORM

This is a Division of Application Ser. No. 08/870,385 filed Jun. 6, 1997 now U.S. Pat. No. 6,274,386. The disclosure of the prior application is hereby incorporated by reference herein in its entirety.

Subject matter of the invention is a reagent preparation for binding components of a sample in the form of a tablet, the use thereof for binding or purifying nucleic acids and a method of preparing a suspension of magnetic particles in a sample, and a method of incorporating magnetic particles in a sample.

A problem which frequently arises in the analysis of liquid samples is that the components to be analyzed are present only in very minute amounts. Moreover, the sample also contains numerous particles which are not to be determined but render the determination less accurate. It is therefore expedient to bind the analytes to a solid phase and remove the particles which are not to be determined together with the liquid. The isolated analytes can then be detected at the solid phase. Recently, especially the inner walls of reaction vessels such as tubes have been used as solid phases. Another option is to add a bead to the reaction vessel which is capable of binding the analyte. The bead size is such that the separation of liquid and beads can be accomplished by simple pipetting. Recently, however, continuously operating instruments have been designed where the analyte is bound to magnetic particles, and the bound analyte together with the magnetic particle are separated from the surrounding liquid with the aid of a magnetic field. The magnetic particles are provided with a surface capable of binding an analyte.

These magnetic particle containing reagent preparations are offered in the form of suspensions to which the analyte-containing liquid to be assayed is added by pipetting. These pipetting steps are subject to deviations commonly found in connection with pipetting procedures. Further, pipetting errors are also difficult to trace back.

It was hence an object of the present invention to eliminate the disadvantages found in the prior art and providing magnetic particles which allow easy dosing.

Subject matter of the invention is hence a reagent preparation for binding components in a sample in the form of a tablet comprising a multitude of particles having a surface to which the components can essentially completely bind and excipients. Another subject matter of the invention is the use of these reagent preparations and a method of preparing magnetic suspensions.

Components are understood to be particulate or molecular material. This includes especially cells, e.g. viruses or bacteria, but also isolated human or animal cells such as leukocytes, then also immunologically active low and high molecular chemical compounds such as haptens, antigens, antibodies, and nucleic acids. Particularly preferred are nucleic acids such as DNA or RNA.

Samples as understood in the invention are for example clinical specimen such as blood, serum, mouth wash liquid, urine, cerebrospinal fluid, sputum, stool, punctate, and bone marrow samples. The sample can also stem from areas such as environmental analysis, food analysis or molecular-biological research, e.g. bacterial cultures, tissue lysates, and products of amplification processes such as PCR.

A tablet as understood in the invention is a solid, formed body, preferably in the form of a disk or a more or less perfectly shaped sphere. Other similar embodiments are also conceivable. Tablets of this kind are commonly known from drugs. A tablet preferably has a defined weight which exceeds 5 mg.

A magnetic particle is a particle made of a material which can be attracted by a magnet, i.e. ferromagnetic or superparamagnetic materials. The invention prefers in particular superparamagnetic particles, especially those that are not premagnetized. Premagnetization as understood here is a process of bringing a material into contact with a magnet to increase resonance. Magnetide ($Fe_3O_4$) or $Fe_2O_3$ are particularly preferred. A magnetic particle is, however, also understood to include materials which contain (smaller) magnetic particles. This includes in particular Iriodin 600 a pigment which is commercially available from Merck (Darmstadt, Germany). The invention prefers in particular particles with an average grain size of less than 100 $\mu$m. A particularly preferred grain size ranges between 10 and 60 $\mu$m. The preferred grain distribution is relatively homogeneous; in particular, there are almost no particles smaller than 10 $\mu$m or larger than 60 $\mu$m. Particles which satisfy this requirement are described for example in WO 90/06045.

An essential element of the invention is the fact that magnetic particles have a surface to which components can bind. This binding can either be specific or relatively non-specific. Specific binding can be achieved by making use of a binding-specific interactions, e.g. antibodies and antigens, antibodies and haptens or complementary nucleic acids. A combination of these interactions is also possible.

A known method of modifying a surface is, for example, the coating of particles with a streptavidin layer. It is thus possible to generate a universal matrix to which specific components can be bound from the sample via conjugates of biotin and a certain antibody, hapten or nucleic acid. The expert, especially one from the field of immunoassays, is familiar with corresponding embodiments.

A relatively unspecific binding is the interaction between a glass-like surface and nucleic acids. The binding of nucleic acids from agarose gel in the presence of sodium iodide in ground flint glass is known from Proc Natl Acad USA 76, 615–619 (1979). U.S. Pat. No. 2,233,169 describes magnetic particles whose glass portion can bind nucleic acids.

The invention proposes that the component to be determined bind essentially completely to the magnetic particles. The expert can easily determine the necessary amount of particles by varying the amount of magnetic particles to be added. As understood in the invention, an essentially complete binding means binding of more than 60%, particularly preferred more than 90% of the component to be bound found in the sample.

Excipients essentially serve to maintain the shape of the tablet, i.e. to link the magnetic particles to form a tablet. Preferred excipients of the invention are those which dissolve rapidly in the sample where the reaction is to take place. As preferred liquid samples are aqueous solutions, it is possible to use those excipients that are usually employed in the manufacture of drugs. Polyethyleneglycol (PEG) and polyvinylpyrrolidon (PVP) are particularly preferred.

DE-A-4406139 describes a magnetic depot drug with improved absorbance of the active components. The tablet contains a disk-like magnet and the active component is released over period of several hours.

The International Journal of Pharmaceutics 119, 47–55 (1995) also describes a tablet with a delayed release of the drug.

STP Pharmasciences Vol 4, 425–430 (1994) describes the manufacture of ferrrite-containing magnetic tablets and their administration to dogs.

Moreover, the tablet of the invention can also contain stabilizing reagents. In a preferred manner, sugars such as D-mannite, trehalose, and sorbite are added.

Surprisingly, magnetic particles, especially those with a glass surface, can be stored in the form of a tablet without visible hydrolysis of the glass and hence without visible elution of the iron from the magnetic portion.

The magnetic particles are preferably glass magnet pigments or polymer magnetic beads or other magnetic particles with a size ranging between 0.1 μm and 100 μm; e.g. those described in DE 19520390.

The preparation can also contain additives to facilitate the binding process of the components. This includes specificity enhancing substances like the above mentioned conjugates; but also substances which modify the sample properties such that the binding of the components to the surface is facilitated. When nucleic acids are used these are chaotropic salts such as guanidinium hydrochloride, sodium iodide, sodium perchlorate or the like. Chaotropic salts of this kind are known from Anal. Biochem. 121, 382–387 (1982) and DE-A 3734442.

The reagent preparation can also contain reagents which convert the components into a form which basically enables a binding process. This includes reagents to lyse compartments, e.g. cells, which contain nucleic acids. Such a reagent is, for example, proteinase K or the above chaotropic salts.

The reagent preparation can also contain pH buffer substances and reagents for dissolving links such as hydrogen bridges, hydrophobic and ion links as well as reagents for the specific detection of substances or indicators as they are known with components of immunoassays.

The following composition has proven to be feasible for a preferred tablet:

| Component | Preferred Amount | Particularly Preferred Amount |
|---|---|---|
| Excipient (e.g. PEG, PVP, Calcium stearate) | 2–10% | 3% |
| Reagents | 0–90% | 87% |
| Magnetic particles | 0.01–50% | 10% |

The tablet of the invention can of course also contain other components, e.g. inert filling agents; the total amount acids up to 100%. The percentages given are weight percentages.

The reagent preparation of the invention in the form of a tablet can be manufactured corresponding to other drugs in tablet form. To accomplish this, all necessary components are thoroughly mixed and aliquots are tabletted in a tablet press. This is accomplished in particular by applying pressure. Tablets of the invention can, however, also be obtained by granulating the mixture of components. For this purpose, a certain amount of the dry mixture is granulated with a solubilizing liquid. Then liquid is again withdrawn from the so obtained granulate. Uniform grain size can be obtained by sieving the granulate.

These manufacturing processes entail a very low coefficient of variation of the tablet weight and hence a high reproducibility when dosing the reagent in the practice. Erroneous dosing is then reduced and easier to trace back. The tablets of the invention can be rapidly dissolved, preferably in less than 30 sec., particularly preferred in less than 1 to 10 sec. while the magnetic particles can be easily and readily dispersed. Tablet form is also expedient with respect to storage. Dosing can even be accomplished manually with the aid of a tablet dispenser. Adulterations which occur in suspensions and are caused by sedimentation of particles have not been observed.

Another subject matter of the invention is the use of the reagent preparation for binding nucleic acids. To accomplish this, the reagent preparation is added to the sample and incubate until (1.) the tablet has dissolved and (2.) the nucleic acids are essentially completely bound to the surface. The tablet can be mechanically moved, if necessary. This increases both the dissolving rate of the tablet and the binding rate of the components.

Another subject matter of the invention is the use of the reagent preparation for purifying nucleic acids. To achieve this, the magnetic particles and the nucleic acids bound thereto are separated from the surrounding sample liquid. This is advantageously accomplished in that a magnetic field is applied to retain the magnetic particles in a vessel or at a defined site of the apparatus; then the sample liquid is removed (by e.g. pipetting or displacement) and, if desired, one or several washing steps with other liquids are performed. If desired, the bound nucleic acids can be separated again from the magnetic particles when suitable conditions are applied. In the case of a glass-like surface, these are low-salt conditions, i.e. the salt contents of the elution solution is less than 100 mmol/l.

Another subject matter of the invention is a method of preparing a suspension magnetic particles in a sample comprising the steps of adding to the sample a tablet containing magnetic particles and soluble excipients and moving the tablet in sample, preferably with the aid of a movable magnetic field. The magnetic field can be moved in that a magnet in the vicinity of the sample is moved back and forth such that the magnetic particles are subject to continuous movement. It is, however, also possible that the vessel containing the sample with the tablet and the magnetic particles is moved with respect to the magnet.

Yet another subject of the invention is a method of incorporating magnetic particles in a sample comprising the steps of providing a dispenser which contains a multitude of magnetic particle-containing tablets and activating the dispenser to release a tablet. Dispensers for providing tablets are commonly used when administering drugs in the form of tablets. They can be used manually for dosing procedures in the method of the invention. It is not absolutely necessary to release only one tablet per sample. It is also possible to release a defined number of tablets, e.g. between 2 and 10, depending on the intended use in the sample.

The following example explain the invention greater detail:

EXAMPLE 1
Preparation of the Glass Magnet Pigment

A sol ($SiO_2$:$B_2O_3$=7:3) was prepared in a 250 ml round flask under constant stirring while observing the following instructions 86.6 ml tetraethylorthosilicate
+7 ml anhydrous, non-denatured ethanol
+14 ml 0.15 M HCl A two-phase mixture is obtained which is stirred at room temperature until one single phase is obtained. Then 37.8 ml trimethylborate are added dropwise. Subsequently the sol is for 2 hours kept at a temperature of 50° C. Then, 14.1 ml of 15 M HCl are added.

After maturing, 22.5 g Iriodin 600 (Black Mica, Merck, Darmstadt, Germany) were added to 150 ml sol under stirring and then coated with a spray-drier (Büchi 190, Mini Spray Dryer).

The powder obtained in the spray-drying process was then subject to temperature treatment under a nitrogen atmosphere. The heating rate was 1 K/min and the dwelling time was 2 hours at the compacting temperature. After compacting, the temperature was lowered down to the temperature of the follow-up treatment; the nitrogen atmosphere was replaced by air and after the follow-up treatment, the powder was cooled down to room temperature. Agglomerates that may have formed were removed by sieving with a 50 μm sieve.

| Parameter | GMP 2 |
|---|---|
| Maturing of the sol at 30° C. (h) | 36 |
| Percentage of pigment of the sol (g/100 ml) | 15 |
| Nozzle temperature (° C.) | 120 |
| Air current of nozzle (%) | 100 |
| Air pressure (bar) | 6 |
| Compacting temperature (° C.) | 534 |
| $O_2$ Follow-up treatment (1 hour) | (300° C.) |

EXAMPLE 2
Tablet Production
Pre-Mixing Process 43.62 g of glass magnet pigment GMP 2 were mixed with 500 g guanidinium hydrochloride and sieved through a 0.2 mm sieve using a GLA-ORV Frewiit sieving machine. The yield amounted to 536.4 g; this corresponds to 98.7%.
Graining 0.674 Tris-HCl and 0.259 g urea were dissolved in 2.2 ml bidest. water. Together with 266.4 g of the pre-mix, the solution was then grained. A total of 7 ml $H_2O$ bidest were added. The resulting granulate was dried in a vacuum at room temperature over a period of 24 hours and subsequently sieved through a 0.6 mm sieve.
Tabletting 246.98 of the granulate were mixed with 7.41 spray-hardened PEG 6000 and tabletted on a Korsch PH106 tablet press with a die size of 5 mm. The yield was 186.63 g or 2902 tablets. The tablets had a weight of 64.32 mg, a hardness of 1.5 kp, a dissolving time in dist. water at room temperature of 6 sec, a wear of 0.8%, and a tablet height of 2.77 mm.

Tabletting machine and die were easy to clean, the bottom dies remained polished, the dies did not exhibit any coat. The mass ran through somewhat slowly resulting in weight CV of 4.65% which could be significantly improved by minor technical measures.

EXAMPLE 3
Storage 10 tablets of example 1 were weighed and added into an open glass vessel and stored open in the lab at room temperature at appr. 50% rF. The weight was monitored over a period of four weeks. There were no weight changes.

EXAMPLE 4
a) PCR Sample Preparation from Human Whole Blood with Magnetic Glass Particles Isolating the Nucleic Acid 10 mg of glass magnet particle GMP 2 were prepared in Eppendorf reaction vessels. 40 μl of proteinase K (20 mg/ml, obtained from lyophilisate) were added to each of 200 μl of thawed whole blood and mixed immediately. Subsequently, 200 μl binding buffer (6 M Guanidine-HCl, 10 mM Tris HCl, 10 mM urea, 30% Triton X-100, pH 4.4) were added, mixed and incubated for 10 minutes at 70° C. After addition of 200 μl i-propanol, the mixture was mixed for 10 seconds on the vortex mixer; the sample was incubated for 20 min. at room temperature and mixed again for 10 seconds as was done before. Magnetic separation was carried out for at least 30 seconds in a Boehringer Mannheim magnet particle separator (Cat. no.: 1641 794). The supernatant was removed and analyzed as described further below.

Using portions of 500 μl washing buffer (20 mM NaCl, 10 mM Tris-HCl, pH 7.5 (25° C.), 70% ethanol), the magnetic particles were washed by mixing for 10 seconds, incubating for 1 min at RT, and mixing again for 10 seconds, and then deposited at the vessel wall using the magnetic particle separator. The supernatant was removed and discarded. The washing procedure was repeated until the washing supernatant was colorless (total of 5 times) Now, the nucleic acids were eluted by mixing 3 times for 10 seconds using 200 μl each time and elution buffer that was preheated to 70° C.; then incubated again at for 10 min. at RT and mixed again for 10 min.
Processing the Supernatant The supernatant obtained after the first binding to the magnetic glass particle was checked for its contents of nucleic acids as follows: The supernatant was transferred into a filter tube (Boehringer Mannheim Cat. no. 1744003, contained in the High Pure PCR Product Purification Kit) and centrifuged for 1 min at 8000 rpm using an Eppendorf table centrifuge). The flow-through was discarded and the filter tube washed 2× with 500 μl washing buffer each time (centrifuged again as before). The filter tube was centrifuged until it was dry and then eluted by repeating the centrifugation and using 2×200 μl 1× eluting buffer preheated to 70° C.
Analysis of the Eluates and the Sample Supernatant 10 μl of sample buffer were added to 50 μl of the eluate and the supernatant processed via the filter tube; 45 μl thereof were then for 90 minutes electrophoretically separated at 120 V in a 0.8% agarose gel.

Various dilutions of the eluates and the processed supernatants were spectroscopically analyzed at 260 and 280 nm using a Uvikon 710 (Kontron).

Using the Expand™ Long Template PCR (Boehringer Mannheim, Cat. no. 1681834), two 5 μl aliquots of the eluates were tested with specific primers for the human tPA gene (expected amplificate length 15 kb).

| mix I | amount per batch | mix II | amount per batch |
|---|---|---|---|
| dNTP, 100 mM each | 1 μl | Expand ™ buffer 10 × | 5 μl |
| primer 1, 200 ng/μl | 1 μl | Expand ™ polymerase | 0.75 μl |
| primer 2, 225 ng/μl | 1 μl | $H_2O$ bidest. | 19.25 μl |
| $H_2O$, bidest. | 17 μl | | |
| | 20 μl | | 25 μl |

Mix I was added into a thin-walled PCR tube, then 5 μl eluate were added, and then mix II was added. The mixture was mixed briefly and 30 μl mineral oil were layered on top of it. The batches were amplified in a Perkin Elmer Themocycler 9600 programmed as follows:

| 2 minutes | 92° C. | |
| 10 seconds | 92° C. | 10 cycles |
| 30 seconds | 65° C. | |
| 12 minutes | 68° C. | |
| 10 seconds | 92° C. | 20 cycles |

| | |
|---|---|
| 30 seconds | 65° C. |
| 12 minutes + 20 seconds per cycle | 68° C. |
| 7 minutes | 68° C. |
| then | 7° C. |

10 μl sample buffer were added to the 50 μl PCR batches and 45 μl thereof were then for 90 minutes electrophoretically separated at 120 V in a 0.8% agarose gel.

b. Use of the Pigments of Example 2 Tabletted According to the Invention 2 tablets of example 2 were added into an Eppendorf reaction vessel, 40 ml proteinase K (20 mg/ml) and 200 μl thawed whole blood (cf. example 4a) were added and immediately mixed for 10 seconds on a vortex mixer. 200 μl of 30% Triton X-100 were added and mixed for 10 min on the vortex mixer. The treatment was then continued as described in example 4.

c. Comparison

Considering commonly accepted deviations, the results for 4a and 4b were identical with respect to both DNA yield in the first elution step and amplificability.

What is claimed is:

1. A method of binding nucleic acids to magnetic particles, comprising:
    Adding to a sample containing nucleic acids a tablet comprising a plurality of magnetic particles having a silica-based glass surface, to which the nucleic acids of said samples can essentially completely bind; and at least one excipient which links the magnetic particles to form a tablet; and thereafter
    Allowing said tablet to contact said sample until said excipient has dissolved and said nucleic acids are essentially completely bound to the surface of the magnetic particles.

2. The method of claim 1, further comprising the step of mechanically moving said tablet to facilitate the dissolving of said excipient in the sample.

3. The method of claim 1, further comprising applying a magnetic field to the sample to retain the magnetic particles and said nucleic acids bound thereto; and separating the magnetic particles and said nucleic acids bound thereto from the remainder of the sample.

4. A method of preparing a suspension of nucleic acid-bound magnetic particles in a sample containing nucleic acids that can bind to the magnetic particles, comprising:
    Adding to the sample a tablet containing a plurality of magnetic particles having silica-bound glass surface, to which the nucleic acid of said sample can essentially completely bind; and at least one excipient which is soluble and links the magnetic particle to form said tablet; and
    Moving the tablet within said sample, to facilitate the dissolution of the soluble excipient in the sample thereby releasing the nucleic acid-bound magnetic particles to form said suspension.

5. A method of incorporating magnetic particles into a sample of nucleic acids, comprising:
    Providing a dispenser containing a plurality of tablet comprising a plurality of magnetic particles having a silica-based glass surface, to which the nucleic acids of sample can essentially completely bind; and at least one excipient which links the magnetic particles to form said tablet;
    Activating the dispenser to release at least one of the tablets into the sample; and
    Permitting the magnetic particles contained in the tablets to disperse in the sample.

6. A method of separating nucleic acid in a sample from the remainder of the sample, comprising:
    Placing a tablet, comprising a plurality of magnetic particles having a silica-based glass surface, to which the nucleic acids in the sample can essentially completely bind; and at least one excipient which links the magnetic particles to form said tablet, in a sample;
    Allowing the nucleic acids in the sample to bind to the surface of the magnetic particles in the tablet;
    Applying a magnetic field to the sample to retain the magnetic particles and nucleic acids bound thereto; and
    Separating the remainder of the sample from the retained magnetic particles and nucleic acids bound thereto.

* * * * *